United States Patent [19]

Moore et al.

[11] Patent Number: 4,502,160
[45] Date of Patent: Mar. 5, 1985

[54] ADJUSTABLE LENGTH PROSTHETIC JOINT IMPLANT

[75] Inventors: William A. Moore, Germantown, Tenn.; Michael M. Lewis, New York, N.Y.

[73] Assignee: Dow Corning Wright, Arlington, Tenn.

[21] Appl. No.: 546,006

[22] Filed: Oct. 27, 1983

[51] Int. Cl.³ .............................................. A61F 1/00
[52] U.S. Cl. .............................................. 3/1.9; 3/1; 128/92 C; 128/92 BC; 128/92 B
[58] Field of Search .................. 403/392, 104, 44, 45, 403/296; 3/1.91, 1.9, 1.911, 1.912, 1.913, 1; 128/92 C, 92 B, 92 BC, 92 R, 92 EB, 92 G

[56] References Cited

U.S. PATENT DOCUMENTS

| 2,822,199 | 2/1958 | Johnson | 403/45 |
| 3,081,116 | 3/1963 | Weiner et al. | 403/44 |
| 4,384,373 | 5/1983 | Sivash | 3/1.91 |

Primary Examiner—Richard J. Apley
Assistant Examiner—David Isabella
Attorney, Agent, or Firm—Howard W. Hermann

[57] ABSTRACT

There is disclosed a surgically implantable prosthetic joint implant adapted for length adjustment after initial surgery to compensate, for example, for growth of a juvenile patient. A stem for bone implantation has a flange for overlying the bone end and a threaded portion for adjusting axially with respect to an overlying sleeve which carries at its extremity an articulating component of the joint. A pin in the sleeve and elongated slot in the stem restrain relative rotation but allow axial relative movement as the stem is urged into or out of the sleeve by rotation of a nut coacting with the threads on the stem while being axially restrained by the sleeve. The nut is described as having a ring of gear teeth to be actuated by an insertable gear-carrying key. An alternative embodiment uses an accessible recessed bolt for moving the stem into or out of the sleeve.

5 Claims, 5 Drawing Figures

ADJUSTABLE LENGTH PROSTHETIC JOINT IMPLANT

BACKGROUND OF THE INVENTION

The present invention relates to surgically implantable joint prostheses and more particularly is directed toward a joint prosthesis suitable for skeletal joints in juvenile patients which provides for adjustment as the patient grows.

Various types of surgically implantable prostheses are available as substitutes for natural skeletal joints which have become damaged by disease or trauma. Substitution by excision of the natural joint and replacement with a prosthesis is now common in connection with virtually all joints in the limbs, including toes, ankles, knees, hips, fingers, wrists, elbows and shoulders. Generally, prostheses for such purposes, particularly in the larger joints, include some type of fixation means for anchoring the prosthetic joint parts into adjacent bone. U.S. Pat. No. 4,384,373 to Sivash even shows an entire thigh bone insert having a hip joint at one end and a knee joint at the other, the prosthesis being composed of telescoping parts to allow adjustment of length at the time of implantation.

A problem exists, however, with presently available prostheses in the case of juvenile patients. As the patient grows, the limb having the prosthesis implanted typically does not grow at the same rate as the opposing limb. If the prosthesis is implanted in the knee, for example, it is common to find one leg shorter than the other. While some physical relief can be obtained with special shoes, for example, there are often psychological implications to the patient which it would be desirable to avoid. Even in adult patients it is occasionally found that due to inability to provide an implant having the exact dimension necessary to precisely replace a damaged joint or due to inaccuracies inherent in surgery adjustment of the length of the implant after the initial surgery would be desirable.

SUMMARY OF THE INVENTION

Accordingly it is an object of the present invention to provide a surgically implantable joint having means for adjusting with minimal surgery the length of the implant after implantation and initial healing.

In accordance with this and other objects there is provided by the present invention a prosthetic joint implant which can be adjusted for length with minimal surgery subsequent to implantation. The implant includes a stem having a first portion adapted for implantation into the intramedullary canal of a bone adjacent the joint, an intermediate portion adapted to overlie the bone end, and a threaded portion. A sleeve overlies at least a portion of the threaded portion of the stem in one end thereof and has affixed at the end opposite the stem the articulating component of the joint. Rotation restraining means such as a pin and elongated slot interconnect the stem and sleeve for preventing relative rotation between stem and sleeve but allowing axial relative movement. Length adjustment means which are axially fixed relative to the sleeve rotatably engage the threads on the stem to urge portions of the stem out of or into the sleeve, thereby lengthening or shortening the length of the device.

In a preferred embodiment the length adjustment means include a nut engaging the threads on the stem but having axial restraining means interconnecting the nut and sleeve. The axial restraining means comprise a circumferential slot in the sleeve cooperating with a pin through the collar on the nut, the collar extending over the end of the sleeve. The collar of the nut may be provided with a ring of gear teeth for cooperation with a gear-carrying key for rotation of the nut to urge the stem into or out of the sleeve as required. An alternative embodiment uses an adjustment bolt to lengthen or shorten the stem. The bolt head is made accessible to the exterior of the prosthesis for use with, for example, a hexagonal wrench.

To use the device, the surgical implantation is carried out in a manner similar to conventional prosthetic joint implant surgery. After the initial surgery has healed if it is found that adjustment is desirable a small incision is made to expose the position for inserting the adjustment tool. The tool is inserted to turn the nut or bolt to lengthen or shorten the implant as desired and the incision is again closed. Thus, the initial surgery is no more complicated than conventional implant surgery and any necessary follow-up surgery for adjusting the implant length is relatively minor.

BRIEF DESCRIPTION OF DRAWINGS

The invention will become better understood by those skilled in the art from a reading of the following detailed description in connection with the accompanying drawings wherein.

DESCRIPTION OF THE PREFERRED EMBODIMENTS

Figure 2:
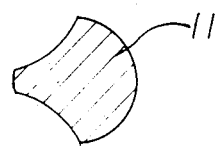
FIG. 2 is a cross-sectional view of the stem of the device shown in FIG. 1 taken along the line 2—2 of that figure.
Figure 4:
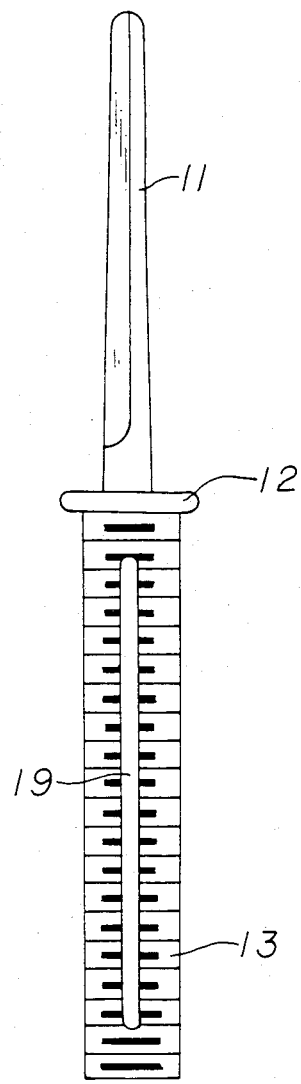
FIG. 4 is a side view in elevation of the stem removed from the embodiment of FIG. 1.

Referring now to the drawings wherein like reference characters designate like or corresponding parts throughout the figures thereof there is shown in FIGS. 1-4 a preferred embodiment of the femoral component of a surgically implantable prosthetic knee joint made in accordance with the present invention. The prosthesis comprises a stem having a first stem portion 11 for implantation in the intramedullary canal of the femur. The intramedullary portion is preferably of noncircular cross-section as shown in FIG. 2 to minimize the possibility of rotation after implantation. The stem has an intermediate collar 12 adjacent the portion 11 which is adapted to overlie at least a portion of the severed bone to provide support therefor and serve to limit growth of bone spurs which occasionally grow from amputated bone in juveniles. At least a portion of the stem extending downwardly from the collar 12 is provided with threads 13 and is located within a sleeve 14. The lower end of the sleeve has affixed thereto an articulating component having condylar portions 16 designed to articulate with the patella and a tibial component and a pair of holes 17 for insertion of a hinge pin whih connects the femoral component to an upstanding post of the tibial component. The femoral and tibial articulating surfaces may be of any conventional shapes and form no part of the present invention.

Restraining means in the form of a pin 18 extending through the sleeve 14 into an elongated slot 19 in the lower portion of the stem restrains relative rotation between the stem and the sleeve. A nut 21 having threads mating with the threads 13 of the stem has a collar overlying the upper end of the sleeve. The upper end of the sleeve 14 is provided with a circular groove 22 into which a pair of pins 23, 24 are inserted through the collar of the nut 21 to provide axial restraining means to prevent axial movement of the nut relative to the sleeve but allow relative rotational movement.

Figure 1:
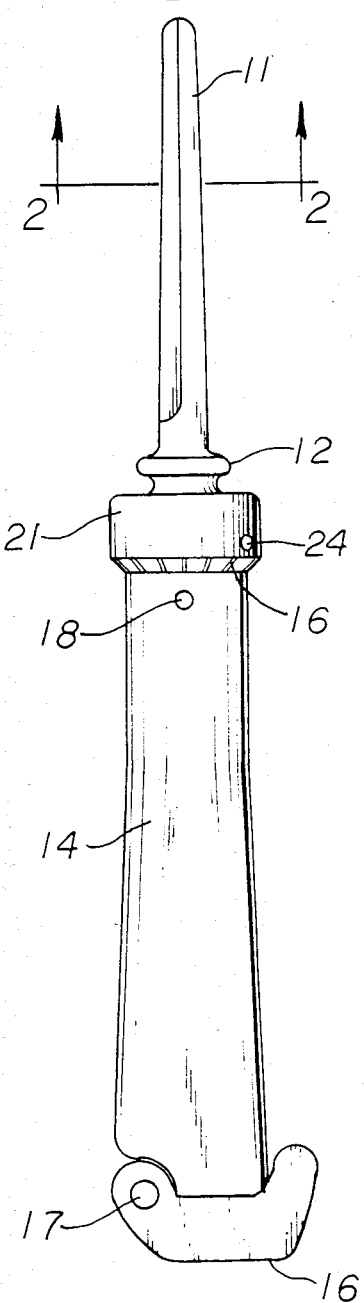
FIG. 1 is a side view in elevation of a preferred embodiment of the invention.
Figure 3:
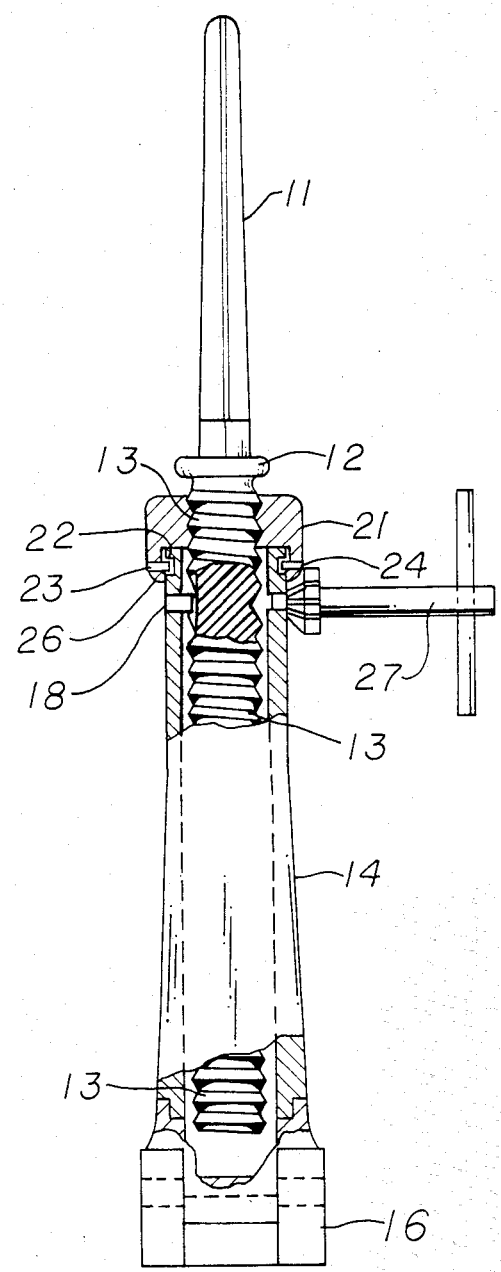
FIG. 3 is an end view, partly in cross-section, of the device shown in FIG. 1.

There are further provided on the collar of the nut a plurality of gear teeth 26 arranged to be operated by a removable gear-carrying key 27 as shown in FIG. 3. The prosthesis can be lengthened or shortened by turning the key 27 which in turn rotates the nut 21 and urges the threaded portion of the stem into or out of the sleeve 14 thereby changing the spacing between the bone end supported by the collar 12 and the articulating portion of the joint. In use, after the initial implantation surgery any required adjustments can be made by making a relatively small incision to expose the key operating position of the gear teeth 26, inserting the key 27 and turning the key as required.

Figure 5:
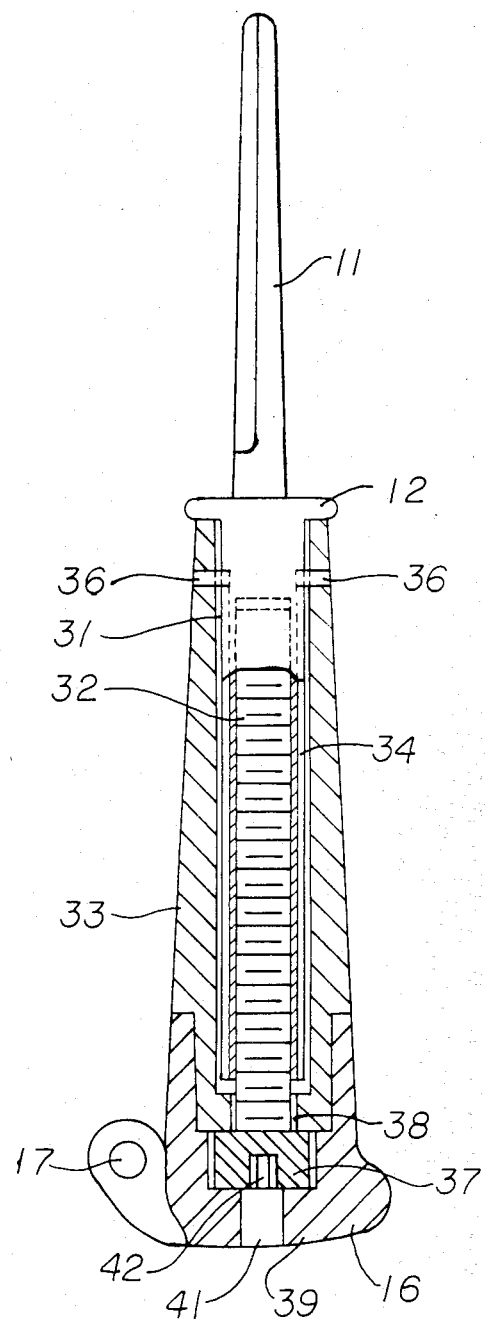
FIG. 5 is a vertical cross-sectional view of an alternative embodiment of the invention.

An alternative construction is illustrated in FIG. 5. In this embodiment the stem again comprises a first stem portion 11 for intramedullary implantation and an intermediate collar 12 for abutting the severed bone end. The lower portion 31 of the stem is made hollow and is internally threaded for coacting with an adjusting bolt 32 positioned axially therein. A sleeve 33 having articulating surfaces 16 and hinge pin hole 17 affixed at its lower extremity surrounds the threaded portion 31 of the stem. The stem portion below the collar is provided with one or more longitudinal grooves 34 into which extend one or more pins 36 extend to provide restraining means against relative rotation between stem and pin but allowing relative axial movement. Axial restraining means for the bolt 32 is provided by confining the bolt head 37 between two abutment portions 38, 39 of the sleeve member. An access opening 41 is provided though the bottom of the sleeve member between the condyles 16 to allow insertion of a hexagonal wrench into a corresponding hexagonal socket 42 in the bolt head 37. Turning the bolt 32 thereby extends or retracts the stem from the sleeve thereby lengthening or shortening the prosthesis. To adjust the device after implantation an incision is made to expose the socket and the drive wrench is inserted into the bolt head and turned as desired.

Obviously other variations and modifications of the preferred embodiments will become apparent to those skilled in the art from a reading of the foregoing. For example, similar designs may be used in connection with prostheses for joints other than the knee. It is to be understood, therefore, that within the scope of the appended claims the invention may be practiced other than as the embodiments specifically described herein.

That which is claimed is:

1. An adjustable length prosthetic joint implant comprising:

a stem having a first portion adapted for implantation in the intramedullary canal of a bone adjacent the joint, an intermediate portion adapted to overlie at least a portion of the bone end and a threaded portion;

a sleeve overlying at least a portion of the threaded portion of the stem in one end thereof and having affixed thereto at the end opposite the stem an articulating component of the joint, rotation restraining means interconnecting the stem and the sleeve for preventing relative rotation therebetween but allowing axial relative movement, said rotation restraining means comprising a logitudinal slot in the portion of the stem which is adapted to be positioned inside the sleeve and a pin member extending through the sleeve and into the slot; and length adjustment means rotatably engaged with the threads on the stem and axially fixed relative to the sleeve whereby rotation of the length adjustment means controls the portion of length of the stem which protrudes from the sleeve.

2. An adjustable prosthetic joint as defined in claim 1 wherein the length adjustment means includes a nut threadedly engaged with the threads on said stem, and axial restraining means interconnecting said nut and said sleeve for preventing axial movement of the nut relative to the sleeve but allowing relative rotational movement.

3. An adjustable prosthetic joint as defined in claim 2 wherein said nut further includes a plurality of gear teeth around a peripheral portion thereof for engagement with a gear-carrying key for rotating said nut.

4. An adjustable prosthetic joint as defined in claim 3 wherein said axial restraining means comprise a circumferential slot in said sleeve, a collar on said nut overlying said slot and a pin member extending through said collar and into said slot.

5. An adjustable prosthetic joint as defined in claim 1 wherein the length adjustment means includes a bolt threadedly engaged with the threads on said stem, and axial restraining means carried by said sleeve for confining the head of said bolt to prevent axial movement of the bolt relative to the sleeve but allow relative rotational movement, said axial restraining means comprising a pair of abutments on said sleeve confining the head of the bolt therebetween, an access opening being provided through the end of the sleeve member to the bolt head for turning the bolt to extend or retract the stem from the sleeve.

* * * * *